United States Patent
Guger et al.

(10) Patent No.: US 11,020,040 B2
(45) Date of Patent: Jun. 1, 2021

(54) APPARATUS AND METHOD FOR ELECTROSTIMULATION OF A TEST SUBJECT

(71) Applicants: Christoph Guger, Piberbach (AT); Guenter Edlinger, Graz (AT)

(72) Inventors: Christoph Guger, Piberbach (AT); Guenter Edlinger, Graz (AT)

(*) Notice: Subject to any disclaimer, the term of this patent is extended or adjusted under 35 U.S.C. 154(b) by 243 days.

(21) Appl. No.: 16/083,045

(22) PCT Filed: Feb. 21, 2017

(86) PCT No.: PCT/AT2017/060036
§ 371 (c)(1),
(2) Date: Sep. 7, 2018

(87) PCT Pub. No.: WO2017/152204
PCT Pub. Date: Sep. 14, 2017

(65) Prior Publication Data
US 2019/0082992 A1 Mar. 21, 2019

(30) Foreign Application Priority Data
Mar. 8, 2016 (AT) .............................. A50189/2016

(51) Int. Cl.
*A61B 5/0484* (2006.01)
*A61B 5/04* (2006.01)
(Continued)

(52) U.S. Cl.
CPC .............. *A61B 5/377* (2021.01); *A61B 5/291* (2021.01); *A61B 5/30* (2021.01); *A61B 5/316* (2021.01);
(Continued)

(58) Field of Classification Search
CPC .............. A61N 1/0531; A61N 1/37247; A61N 1/0476; A61N 1/0456; A61N 1/36185;
(Continued)

(56) References Cited

U.S. PATENT DOCUMENTS

2002/0095097 A1 7/2002 Drongelen
2002/0147411 A1 10/2002 Lutz et al.
(Continued)

OTHER PUBLICATIONS

Wheeler J., et al.: "An implantable 64-channel neural interface with reconfigurable recording and stimulation". Aug. 25, 2015, pp. 7837-7840.

*Primary Examiner* — Christine H Matthews
*Assistant Examiner* — Joshua Daryl D Lannu
(74) *Attorney, Agent, or Firm* — Laurence A. Greenberg; Werner H. Stemer; Ralph E. Locher

(57) ABSTRACT

A method and an apparatus provide electro stimulation to a test subject. A number of electrodes are connected to the brain of a test subject, wherein the voltages present on the individual electrodes are measured and analyzed after the delivery of a stimulus. During a preselection based on the analysis, individual electrodes are selected for the delivery of a stimulus, wherein one electrode is selected from the individual preselected electrodes and the stimulus is delivered to the brain by the electrode. Accordingly, in the analysis using the measurement signals during the preselection, the signals present on the electrodes are examined, in particular exclusively examined, for the presence of signal power or signal energies in the range from 60 Hz to 1 kHz, in particular between 60 Hz and 180 Hz.

22 Claims, 4 Drawing Sheets

(51) Int. Cl.

| | |
|---|---|
| *A61B 5/0478* | (2006.01) |
| *A61B 5/048* | (2006.01) |
| *A61N 1/04* | (2006.01) |
| *A61N 1/05* | (2006.01) |
| *A61B 5/377* | (2021.01) |
| *A61B 5/00* | (2006.01) |
| *A61N 1/372* | (2006.01) |
| *A61B 5/30* | (2021.01) |
| *A61B 5/291* | (2021.01) |
| *A61B 5/316* | (2021.01) |
| *A61B 5/374* | (2021.01) |
| *A61N 1/36* | (2006.01) |

(52) U.S. Cl.
CPC ............ *A61B 5/374* (2021.01); *A61B 5/4064* (2013.01); *A61B 5/7203* (2013.01); *A61B 5/725* (2013.01); *A61B 5/7217* (2013.01); *A61B 5/7475* (2013.01); *A61N 1/0456* (2013.01); *A61N 1/0476* (2013.01); *A61N 1/0531* (2013.01); *A61N 1/37247* (2013.01); *A61B 2562/0209* (2013.01); *A61B 2562/046* (2013.01); *A61N 1/36185* (2013.01)

(58) Field of Classification Search
CPC ... A61B 5/7203; A61B 5/725; A61B 5/04014; A61B 5/7475; A61B 2562/046; A61B 5/4064; A61B 5/0484; A61B 2562/0209; A61B 5/048; A61B 5/04004; A61B 5/0478; A61B 5/7217
See application file for complete search history.

(56) References Cited

U.S. PATENT DOCUMENTS

| | | |
|---|---|---|
| 2009/0082691 A1 | 3/2009 | Denison et al. |
| 2011/0264165 A1* | 10/2011 | Molnar ............. A61N 1/36185 607/45 |
| 2012/0253421 A1 | 10/2012 | Gliner et al. |

* cited by examiner

APPARATUS AND METHOD FOR ELECTROSTIMULATION OF A TEST SUBJECT

BACKGROUND OF THE INVENTION

Field of the Invention

The invention relates to an apparatus for electrostimulation of a person comprising a number of electrodes applicable to the human brain.

It is necessary in a variety of medical applications to identify individual regions of the brain and the associated functions thereof. In particular, it can be advantageous for specific applications to recognize regions of the brain in which specific motor, auditory, visual, sensory, or other processes are controlled.

Electrostimulation apparatuses are known from the prior art, which have a plurality of electrodes which are applied directly to the human brain. In the course of the procedure known from the prior art, regions of the human brain are analyzed by applying a large number of electrodes to the human brain. Subsequently, stimuli in the form of voltages are applied to individual adjacently located electrodes, whereby stimuli in the form of electrical currents flow through the human brain. This excitation has the result that the test subject, to whose brain the electrodes are applied, has specific perceptions/thoughts or carries out specific physical movements. In order to identify the position of specific brain areas, which fulfil specific functions, using the measures known from the prior art, it is necessary to activate or stimulate all electrodes applied to the brain and subsequently wait for the reaction of the test subject. In particular, it can be necessary to amplify the stimulus in the course of the application in order to induce a reaction in the test subject. This procedure is extremely complex and time-consuming and additionally has the disadvantage that increased epileptic seizures can be triggered in patients who tend toward epileptic seizures. Furthermore, it can be difficult in the case of children or patients to obtain correct descriptions of perceptions.

SUMMARY OF THE INVENTION

The object of the invention is therefore to provide a method which manages overall with a lesser number of stimuli on the human brain and nonetheless to ensure the advantageous identification of the regions in the human brain which are responsible for a specific function. It is also the object of the invention to provide an apparatus, using which areas of the human brain which are responsible for a specific function, can be found in a rapid and simple manner.

The invention achieves this object in an apparatus of the type mentioned at the outset with the features of the main patent claim. In this case, in an apparatus for electro stimulation of a test subject comprising a number of electrodes applicable to the human brain for triggering specific electrical stimuli on the human brain,
  wherein a control unit comprising a stimulation unit is provided, using which electrical stimuli are applicable to individual or multiple electrodes,
  wherein the control unit has a measuring unit connected downstream of the electrodes for determining the voltages applied to the individual electrodes,
  wherein the control unit has an analysis unit, which analyzes the individual measurement signals registered using measuring electrodes and selects individual ones of the electrodes for the emission of a stimulus in the scope of a preselection on the basis of this analysis, and
  wherein the control unit has a selection and actuating unit, which is actuable in particular by a human, for selecting one or more electrodes among the electrodes preselected by the analysis unit and also for the emission of a predefined electrical stimulus at the electrode(s) selected in this manner by the stimulation unit, which is connected downstream of the analysis unit and is connected upstream of the stimulation unit, it is provided that the analysis unit is designed for the purpose, during the preselection, of examining the measurement signals at the measuring electrodes, in particular exclusively, for the presence of signal powers or signal energies in the range of 60 Hz to 1 kHz, in particular between 60 Hz and 180 Hz.

A particularly simple overview of the analysis results is achieved by the selection and actuating unit having a display unit, which represents the electrodes and also the analysis results ascertained by the analysis unit, in particular the preselection results, on the basis of the analysis for the individual electrodes at positions of the display unit graphic visualizations of the analysis results.

A simple review of the previously achieved analysis results is possible by
  the selection and actuating unit having individual selection or actuating elements in the region of the display unit,
  the selection or actuating elements each being associated with one electrode and being arranged on the display unit in the region of the position at which the graphic visualizations for the relevant electrode are represented, and
  the selection or actuating elements being designed for selecting the electrode associated therewith for the emission of a stimulus or for the emission of a stimulus using the relevant electrode.

A particularly targeted stimulation of specific brain regions can be achieved by the stimulation unit applying a DC-free stimulus to the electrodes.

To damage the human brain as little as possible, it can be provided that the stimulation unit limits the DC component of the current of the stimulus, and wherein in particular the current curve of the stimulus has a square, triangular, or sinusoidal curve.

To achieve an automatic analysis of the brain regions, it can be provided that a registration unit for registering the reaction of the test subject is provided and is connected to the control unit, wherein the registration unit is formed in particular by a microphone for registering speech of the test subject or by a detector for registering movements of the test subject or is designed to register electrophysiological signals.

To enable the response of individual brain regions at different stimulus threshold values and avoid overstimulation of the brain, it can be provided that the stimulation unit is designed for the purpose of applying stimuli of differing, in particular rising, strengths and/or durations to the individual electrodes.

For manual stimulation, it can be provided in this case that the stimulation unit is designed for the purpose of emitting the individual stimuli, in particular in rising sequence, upon manual actuation or automatically.

For automated stimulation, it can be provided that the control unit activates the stimulation unit to emit stimuli in rising sequence until the registration unit establishes a reaction of the test subject or the current limit is reached.

To be able to advantageously delimit individual functions of the human brain from the general activity of the human brain, it can be provided that the control unit is designed to carry out a base measurement by means of the analysis unit, during which the test subject executes a reference activity, and to store the analysis results—associated with the respective measuring electrode—ascertained in this case as reference values or a reference signal in a reference memory and keep them available, and that the analysis unit has a comparison unit, which compares the individual ascertained analysis values to the stored reference values, wherein the analysis result for each individual electrode specifies how much the ascertained analysis values differ from the reference values associated with the respective electrode.

It can particularly advantageously be provided for recording individual voltages and individual points of the human brain that the individual electrodes are arranged in one grid or multiple grids, wherein in particular the electrodes are arranged in a predefined structure within the respective grid, and/or each of the electrodes except for the edge electrodes has a predefined number of adjacent electrodes, which are arranged at a predetermined position in relation to the respective electrode and/or have equal spacing from one another.

It can particularly advantageously be provided in the individual electrodes and/or in the arrangement of the electrodes in relation to one another that a) the individual electrodes are formed equivalently in relation to one another, and/or b) the individual electrodes arranged within a grid are formed equivalently in relation to one another, and/or c) the electrodes within a grid are arranged in a square or hexagonal structure.

An improvement of the voltages ascertained by the electrodes can be achieved by a separate filter being connected downstream of each of the electrodes, which filter is connected upstream of the analysis unit or the measuring unit and is designed a) if a signal energy which exceeds or falls below a predefined threshold value or a signal form deviating from a setpoint form by more than a predefined threshold value is present, to suppress the relevant signal and not relay it to the analysis unit, and/or b) to filter out signal components below a limiting frequency of 1 Hz to 5 Hz, and/or c) to subtract the mean value of all simultaneously measured signal values of all electrodes, in particular only within the same grid, from the measured value of the relevant electrode, d) to subtract the possibly weighted mean value of all simultaneously measured signal values of all adjacent electrodes to the relevant electrode, in particular only within the same grid, from the measured value of the relevant electrode, wherein in a square grid of electrodes, the following in particular are considered to be adjacent electrodes:

i) the four electrodes directly adjoining an electrode, ii) the eight electrodes surrounding an electrode, wherein possibly the individual adjacent electrodes are weighted with a weighting factor dependent on the distance thereof from the electrode, iii) those four electrodes within a square grid, the one coordinate position of which deviates by two from the relevant coordinate position of the electrode, and the other coordinate position of which corresponds to the relevant coordinate position of the electrode.

A particularly preferred refinement of the invention, using which measured values can be produced in real time, provides that the analysis unit is designed to produce continuously derived measured values for each electrode, wherein measured values produced within a predefined period of time are combined into windows, in particular having a length of 20 ms to 2 seconds, and the analysis unit is designed, in particular by means of FFT or autoregressive models, such as preferably LMS, recursive least square, or Kalman filters of 5 to 50 order, to ascertain the signal energy of the signal within the window in a frequency range having a lower frequency of 60 Hz to 100 Hz and an upper frequency in a frequency range of 150 Hz to 1 kHz, and to produce an analysis signal therefrom, and optionally to produce a reference signal in the scope of the base measurement, and possibly the analysis unit does not use frequency ranges within the predefined window, which lie in a range around the network frequency or a multiple of the network frequency for the formation of the signal energy.

For the advantageous detection of coherent networks, one preferred refinement of the invention provides that the control unit is designed to emit a stimulus in the region of an electrode, in particular using a voltage stimulus having a frequency between 1 Hz and 100 Hz, and the control unit is designed, after the emission of the stimulus at all or a number of electrodes a) to detect evoked potentials in the emitted signal of the respective electrode, or b) to detect the band power of the emitted signal of the respective electrode, in particular in the range between 60 Hz and kHz, and the control unit in this manner represents all electrodes or the brain regions registered by the electrodes in which an evoked potential or an elevated band power in the range between 60 Hz and 1 kHz exists as a result of the stimulus.

One particularly preferred embodiment of the invention will be described in greater detail on the basis of the following figures of the drawings.

DESCRIPTION OF THE INVENTION

Figure 1:
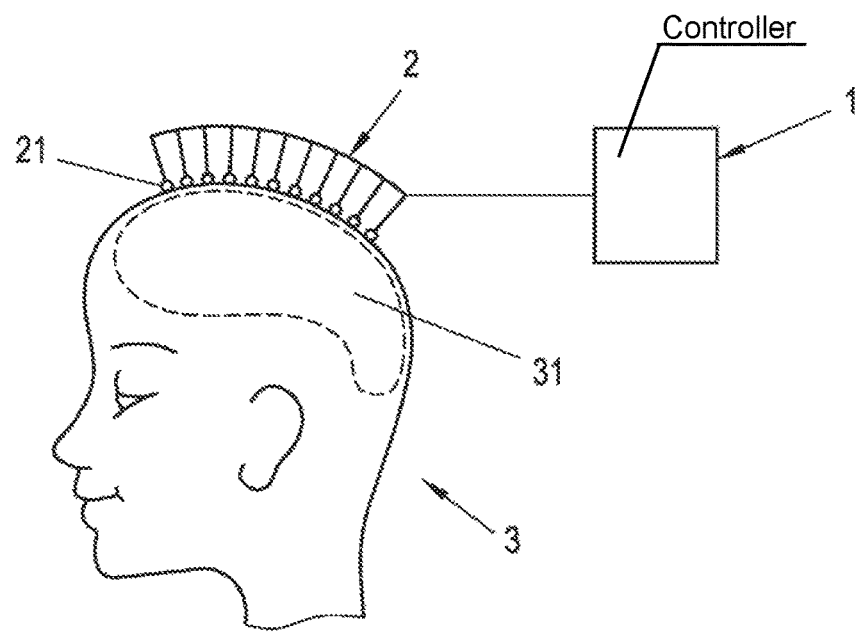
FIG. 1 is an illustration of an electrode arrangement having a number of electrodes which is applied to a brain of a test subject according to the invention.
Figure 8:
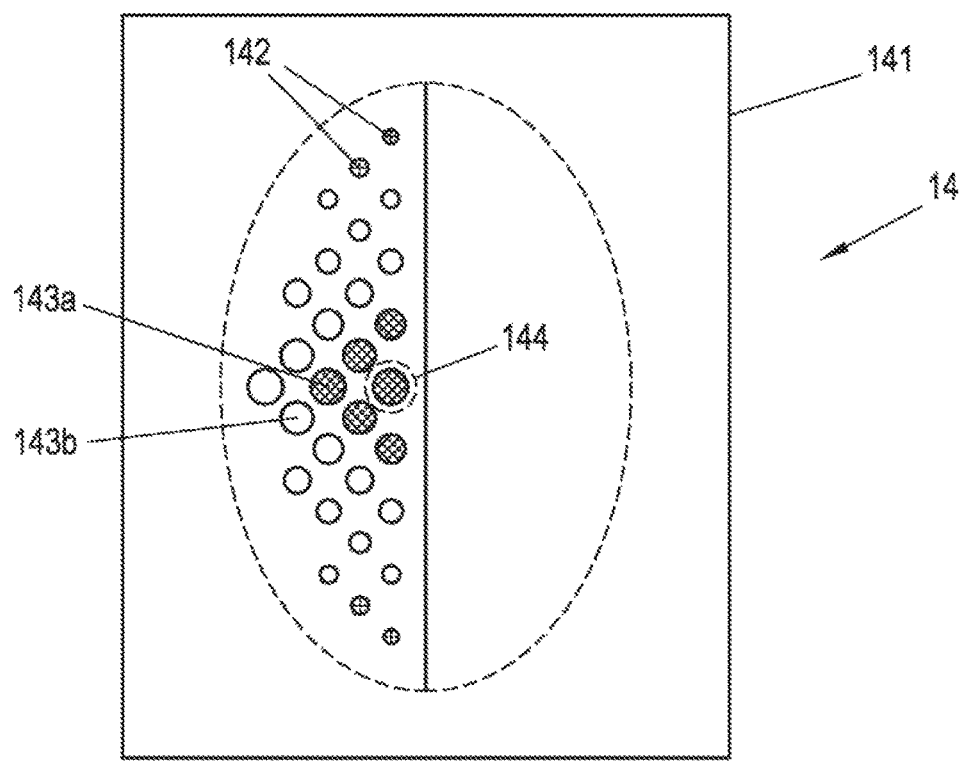
FIG. 8 is an illustration showing a display on a display unit.
Figure 2:
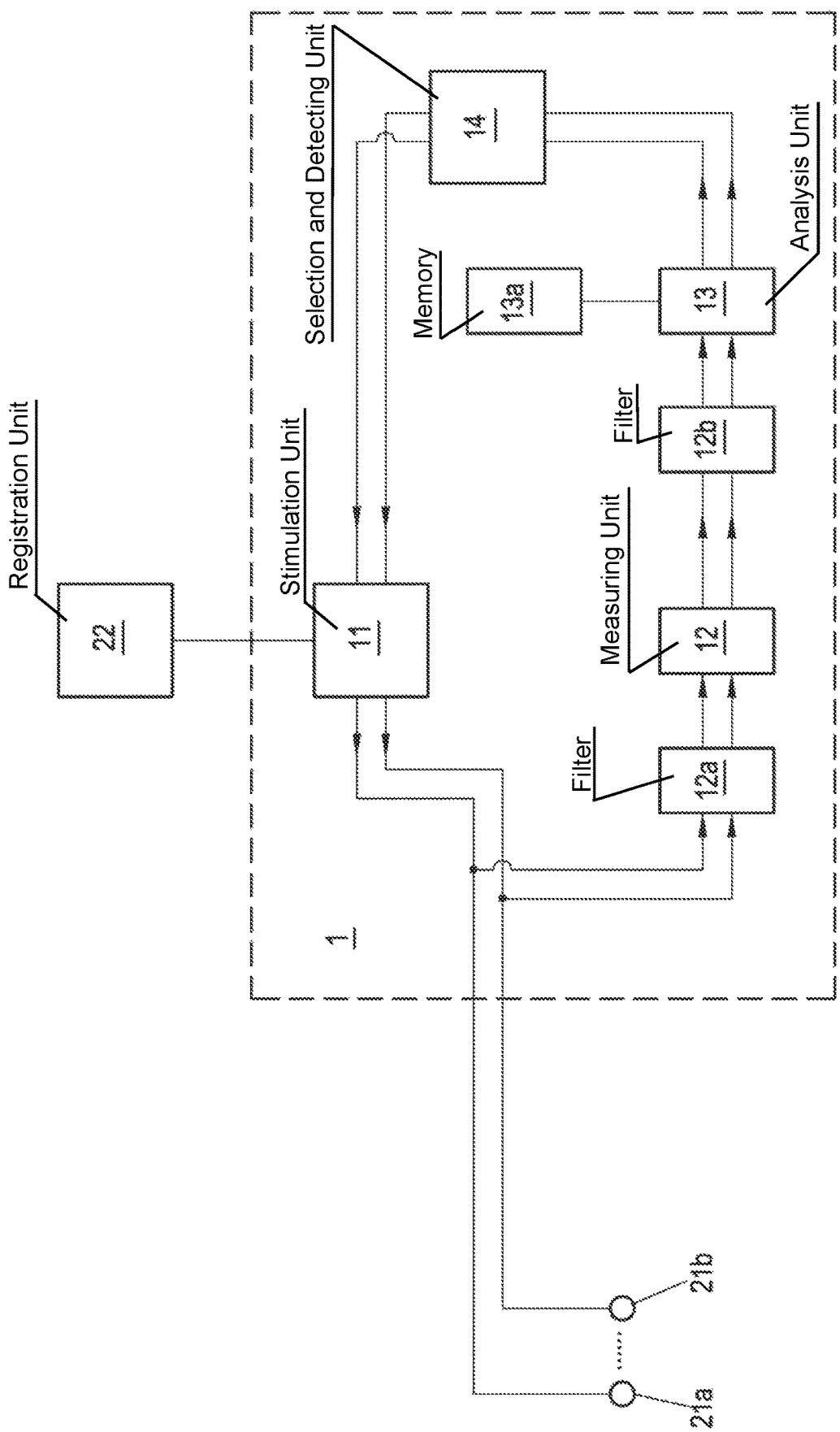
FIG. 2 is a block diagram of a control unit shown in FIG. 1.
Figure 3:
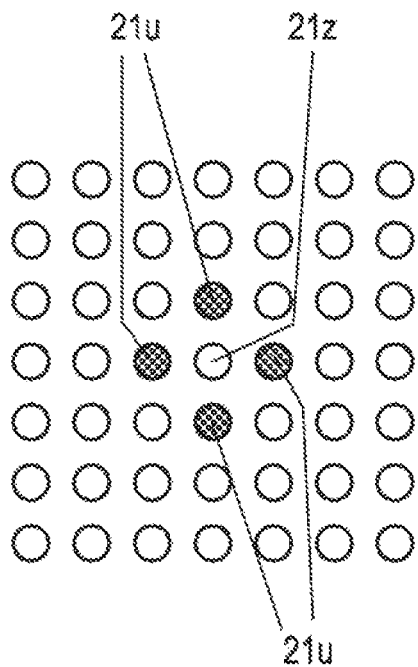
FIGS. 3 to 5 are illustrations showing different filters for preprocessing measurement signals.
Figure 4:
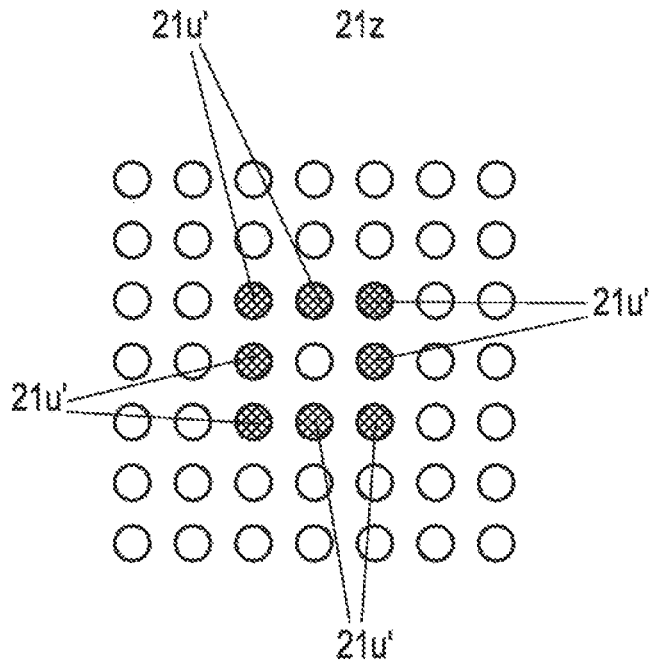
Figure 5:
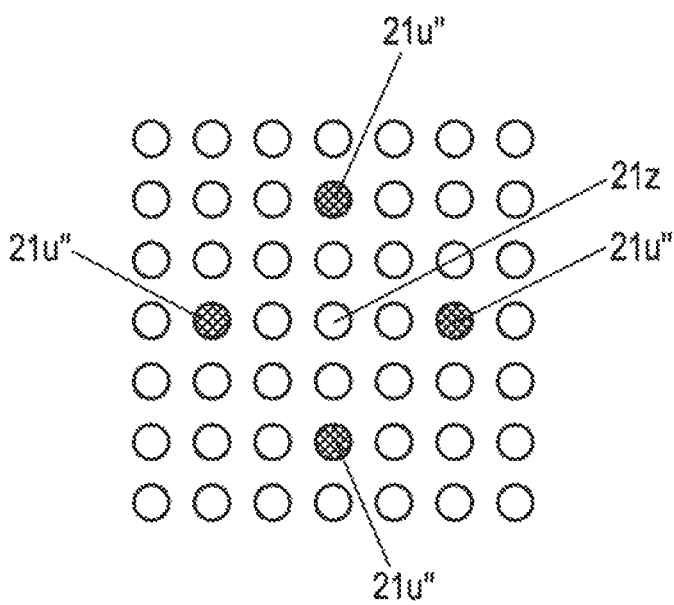
Figure 6:
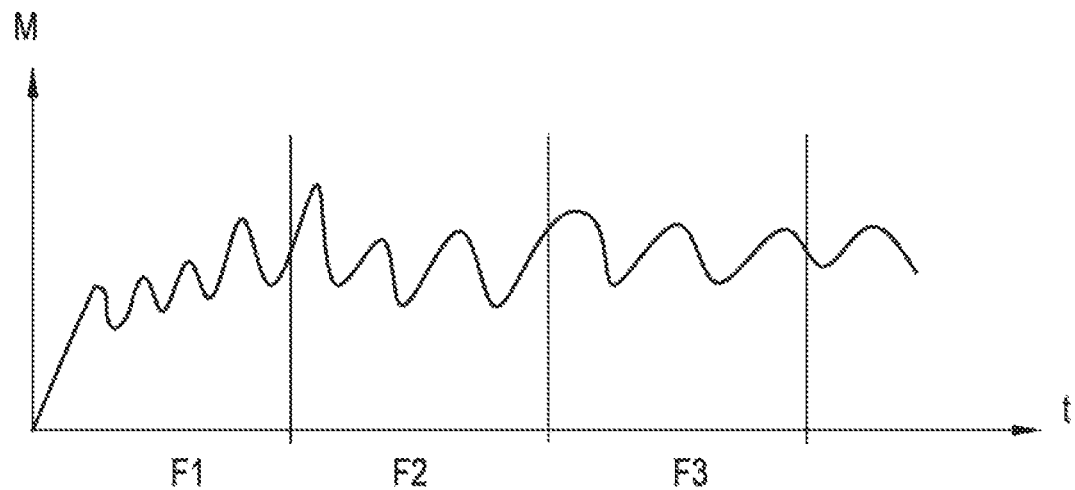
FIG. 6 is a graph showing a production of windows from the measurement signals.
Figure 7:
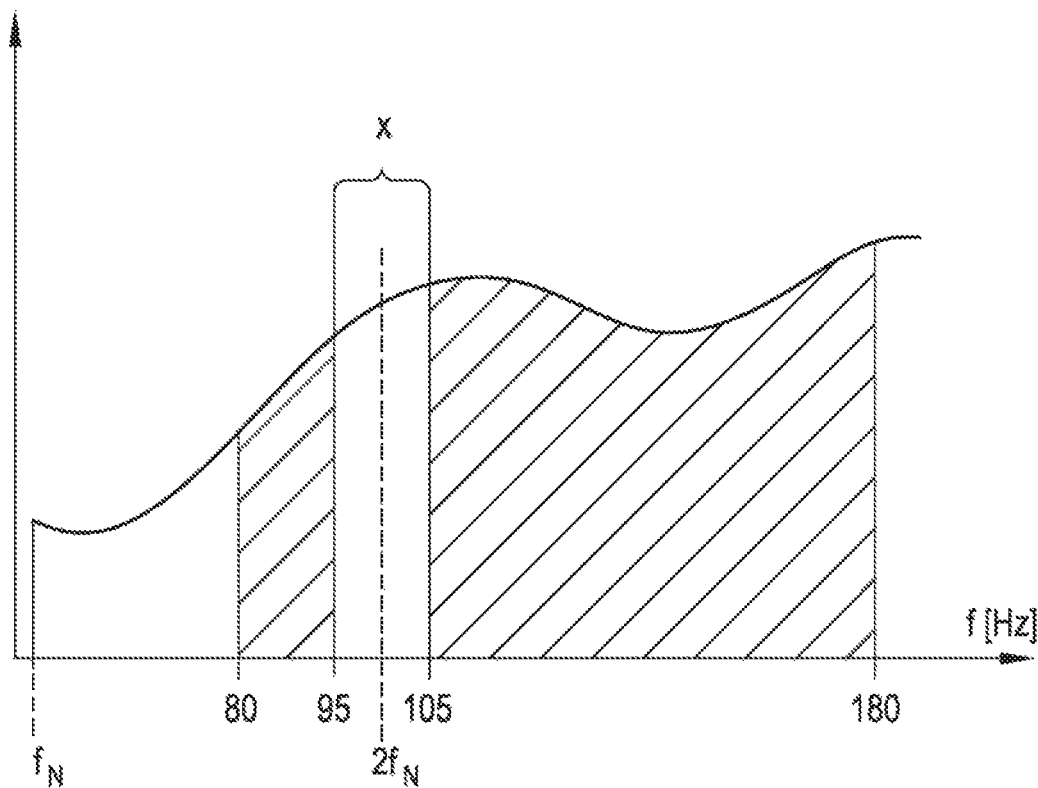
FIG. 7 is a graph showing a determination of signal energy for a window.

FIG. 1 shows an electrode arrangement 2 having a number of electrodes, which is applied to the brain of a test subject. The electrode arrangement is connected to a control unit. FIG. 2 shows a schematic illustration of the control unit of FIG. 1. FIGS. 3 to 5 show different filters for preprocessing the measurement signals. FIG. 6 shows the production of windows from the measurement signals. FIG. 7 shows the determination of the signal energy for a window. FIG. 8 schematically shows the display on a display unit.

An apparatus for electrostimulation of the brain 31 of a test subject 3 is shown in FIG. 1. This apparatus comprises a number of electrodes 21 applicable to the human brain 31, which are combined to form an electrode arrangement 2. This electrode arrangement 2 is connected to a control unit 1.

In principle, the possibility exists in the case of the electrodes 21 applied to the human brain of both measuring individual brain currents via the electrode 21 and analyzing the measurement signals M thus ascertained. On the other hand, however, there is also the possibility of emitting electrical stimuli S via the electrodes 21 to the human brain 31.

The electrodes 21 can be arranged either in one grid or in multiple grids independent of one another, wherein the individual electrodes 21 are arranged in a predefined structure within the respective grid. It is advantageously provided in this case that each of the electrodes 21 with the exception of the edge electrodes has a predefined number of adjacent electrodes, wherein the respective adjacent electrodes 21 are arranged in a predetermined position in relation to the respective electrode 21. Adjacent electrodes 21 preferably have equal spacing from one another within the grid.

Particularly simple implementations of grids can be achieved in that the individual electrodes 21 are formed equivalently to one another, or the individual electrodes 21 arranged within a grid are formed equivalently to one another. The electrodes 21 can be arranged in a square or hexagonal or other regular structure within a grid.

To be able to correctly depict the geometry of the individual grids, different processing programs can be selected, which enable a geometric depiction of the electrode grid and a representation in the correct location of the individual electrodes.

The control unit 1 shown in greater detail in FIG. 2 comprises a stimulation unit 11, which is capable of emitting electrical stimuli S at the individual electrodes 21 of the human brain 31. In addition, the control unit 1 also comprises a measuring unit 12 connected downstream of the electrodes 21. Using this measuring unit 12, individual measurement signals M applied at the electrodes 21 can be ascertained and further processed in the form of voltages. The measurement signals M thus ascertained and/or measured by the measuring unit 12 are supplied to an analysis unit 13, which analyzes the individual measurement signals M applied at the measurement electrodes 21 and carries out a preselection on the basis of this analysis. In this analysis, individual electrodes 21, at which special properties have been established in the signals on the basis of the analysis, are selected for the emission of a stimulus S. It can also be advantageous to apply a stimulus S to surrounding electrodes 21, in order to be able to study the brain region more accurately. Such a selection preferably takes place in that the measurement signals M applied at the electrodes 21 are analyzed as to whether elevated signal energies are present in a specific frequency range between 60 Hz and 1 kHz, in particular between 60 kHz and 170 Hz.

A separate filter 12a, 12b can be connected downstream of the measuring unit 12 for each of the electrodes 21. This filter 12a can be arranged either in the signal path before the measuring unit or in the signal path between the measuring unit 12 and the analysis unit 13. If the filter 12a is arranged before the measuring unit 12, the filter 12a can preferably be designed as an analog filter 12a. In the signal path between the measuring unit 12 and the analysis unit 13, the filter 12b can preferably be designed as a digital filter 12b.

One possible embodiment of a filter 12a, 12b suppresses the relevant signal if a signal energy is present in the measurement signal M which exceeds or falls below a predefined threshold value or in the event of a signal form of the measurement signal M which deviates from a predefined setpoint form by more than a predefined threshold value. In this case, this signal is not relayed to the analysis unit 13, and possibly also not to the measuring unit 12.

Additionally or alternatively, a filter 12a, 12b can also be arranged in the signal path before the measuring unit 12 or between the measuring unit 12 and the analysis unit 13, which filters out signal components below a predefined limiting frequency. This limiting frequency can be selected between 0.1 Hz and 5 Hz.

A further possibility for the functionality of an additional or alternative filter 12a, 12b is to subtract the mean value of all simultaneously measured signal values of all electrodes 21 from the measured value of the relevant electrode 21. This enables a suppression of influences which voltage variations cause on all electrodes 21. If, as described in the following exemplary embodiment, multiple grids of electrodes 21 are used, a filter 12a, 12b can be designed for the purpose of subtracting the mean value of all simultaneously measured signal values of the electrodes 21 only within the same grid from the individual measured values of the relevant electrodes 21.

In addition, the proximity of individual adjacent electrodes 21u within the electrode arrangement 2 and/or within an electrode grid can be utilized in order to suppress effects in the surroundings around an electrode 21z. In this case, the possibility exists of subtracting a mean value of all simultaneously measured signal values of all adjacent electrodes 21u of a relevant electrode 21 from the measured value of the electrode 21, in order to ascertain a filter value in this manner. If the electrode grid is formed as a square electrode grid, i.e., the electrodes 21 within an electrode grid each include a right, a left, an upper, and a lower adjacent electrode 21u, preferably the following filter measures can be carried out using adjacent electrodes.

The mean value can be ascertained by averaging the electrodes 21u directly adjoining the respective electrode 21z (FIG. 3). In this case, the filter value is computed by subtracting the total of the measured signal values of the adjacent electrodes divided by 4 from the measured signal value. The value thus ascertained substantially corresponds to the discretely ascertained Laplace operator or a multiple of the discretely ascertained Laplace operator.

Alternatively, the possibility also exists of using the eight adjacent electrodes 21u' surrounding an electrode 21z for ascertaining the mean value in a square electrode grid (FIG. 4). In this case, those adjacent electrodes 21u' which are located diagonally in relation to the central electrode 21z can be weighted with a lesser weighting factor. In particular, this weighting factor can be dependent on the spacing of the adjacent electrodes, and therefore diagonally located adjacent electrodes 21u' are weighted more weakly by a factor of 1 divided by $\sqrt{2}$ than directly adjoining adjacent electrodes 21u'.

In addition, the possibility also exists of using, instead of the four electrodes 21u directly adjoining the electrode 21z, those four electrodes 21u'' within a square grid for the determination of the mean value, the one coordinate position of which deviates from the relevant coordinate position of the electrode 21z by two, and the other coordinate positions of which corresponds to the relevant coordinate position of the middle electrode (FIG. 5).

A preferred functionality of the analysis unit 13 will be described in greater detail hereafter:

The analysis unit 13 is designed for the purpose of processing continuously derived and at best filtered measured values for each individual electrode 21, wherein measured values produced within a predefined period of time are combined into windows (FIG. 6). In one preferred embodiment of the invention, these windows $F_1$, $F_2$, $F_3$ have a length of 200 ms. However, it is readily possible in principle to also produce windows having a length of 20 ms up to 15 seconds. Within these windows, the measured values are sampled at a sampling frequency of 1000-5000 Hz.

The analysis unit 13 is designed for the purpose of ascertaining the signal energy of the signal within the window in a frequency range having a lower frequency of between 60 and 100 Hz and an upper frequency of between 150 Hz to 1 kHz. A signal energy is respectively specified around each window $F_1$, $F_2$, $F_3$ having a predefined duration. The computation of the signal energy can be ascertained, for example, by means of FFT or by means of autoregressive models, for example LMS, recursive least square, or Kalman filters of between 5 and 100 order.

An analysis value, which specifies the signal energy in the relevant window $F_1$, $F_2$, $F_3$, is available for each window $F_1$, $F_2$, $F_3$. The individual analysis values are combined into an analysis signal A, which has a respective analysis value in the form of the signal energy for each window.

In one preferred embodiment of the invention, frequency ranges within a predefined frequency window, which are in a range around the network frequency or a multiple of the network frequency, are not used for the formation of the signal energy. In the case of a network frequency of 50 Hz, this can preferably take place, for example, in the range of twice the network frequency, i.e., in the range of 100 Hz, wherein energies in the range of, for example, between 95 Hz and 105 Hz are filtered out in the determination of the signal energy (FIG. 7).

One particularly preferred type of the analysis of the incoming measured values can be performed by carrying out a base measurement, during which the test subject 3 executes a mental reference activity, for example, relaxes or thinks of nothing. By means of the individual electrodes 21, analysis values are derived from the measurement signals M as described above, wherein these values are associated with the individual electrodes 21 and are subjected to the analysis of the analysis unit 13. The analysis values derived from the measurement signals M are stored in a reference memory 13a and made available therein. The reference memory 13a is connected to the analysis unit 13. The analysis unit 13 additionally has a comparison unit, which ascertains the voltages ascertained at the electrodes 21 in the case of specific mental activities and derives analysis values therefrom. These values are compared to the reference values stored in the reference memory 13a. An analysis result is ascertained on the basis of the comparison, which specifies for each individual electrode 21 how much the ascertained measurement signals differ from the reference values associated with the respective electrode 21.

The analysis unit 13 can particularly preferably be designed such that it derives the signal energy for the individual time window from the signal generated during the base measurement, as shown in FIG. 8, and generates a reference signal R therefrom, which it stores in the reference memory 13a. In the course of this base measurement, a separate reference signal R is stored for each individual electrode 21, which specifies which electrical signals are emitted by the brain of the test subject 3 during a reference activity.

The analysis unit 13 is furthermore designed for the purpose of ascertaining coefficients k, which specify for each electrode 21 whether the signal derived from the reference signal R for the relevant electrode 21 and the analysis signal A derived from the instantaneously registered measurement signal M differ from one another. The analysis unit 11 keeps such a coefficient k available for a number of electrodes 21, in particular for all electrodes 21. It is particularly preferably possible that the analysis unit 13 scales the present coefficients k such that all coefficients k are divided by the same maximum coefficient $k_{max}$. Alternatively, the possibility also exists of weighting the individual coefficients k using the same weighting value such that the total of all coefficients k of all electrodes 21 has a predefined value, for example, 1.

One particularly preferred variant for determining whether a reference signal R deviates from an analysis signal A ascertained in the course of a further analysis will be described in greater detail hereafter. For this purpose, the respective values are used for the signal energy which were ascertained by the analysis unit 13 in the scope of the base measurement for the reference signal R, on the one hand, and those values which were ascertained in the course of the analysis of the respective present measurement signal S, wherein the analysis signal A thus ascertained also in turn has available individual values for the signal energy for individual time windows $F_1$, $F_2$, $F_3$. A number of signal energies, which were ascertained in the course of the base measurement, and also a number of signal energies, which were ascertained in the course of the present measurement, are thus provided. In a first step, number pairs are produced, the first value of which is the respective signal energy in the course of the measurement or base measurement, and the second value of which specifies whether the respective signal energy originates from the measurement or from the base measurement. For example, for the case in which the signal energy originates from the base measurement, the value −1 can be assigned and for the case in which the signal energy originates from the measurement, the value +1 can be assigned. The respective values used are not important for the further computations, as long as they may be numerically differentiated well from one another.

It can be specified easily by the squared correlation coefficient $r^2$ whether the signals of the base measurement may be differentiated well from the signals of the present measurement.

$$r^2 = \frac{\text{cov}(x, y)^2}{\text{var}(x)\text{var}(y)}$$

The number of the signal energies ascertained in the course of the base measurement is denoted by $n_1$, the number of the signal energies ascertained in the course of the present measurement is denoted by $n_2$. A simpler possibility for determining the correlation coefficients in a numerically efficient manner is to individually store the total of the individual signal energies $X_i$ and the total of the squares of the individual signal energies separately according to whether they have been ascertained in the course of the base measurement or in the course of the present measurement and keep them in reserve.

$$s_k := \sum_i x_i^{(k)}, \; q_k := \sum_i x_i^{(k)2}$$

The values of the covariance cov (x, y) and the variance var (x) required for the computation of the correlation coefficients k can be ascertained from the present totals and square totals as follows:

$$\text{cov}(x, y) = \frac{s_1 - s_2}{n_1 + n_2} - \frac{(s_1 + s_2)(n_1 - n_2)}{(n_1 + n_2)^2} = 2\frac{s_1 n_2 - s_2 n_1}{(n_1 + n_2)^2}$$

$$\text{var}(x) = \frac{q_1 + q_2}{n_1 + n_2} - \frac{(s_1 + s_2)^2}{(n_1 + n_2)^2}$$

$$\text{var}(y) = 1 - \frac{(n_1 - n_2)^2}{(n_1 + n_2)^2} = \frac{4 n_1 n_2}{(n_1 + n_2)^2}$$

The correlation coefficient thus results as follows:

$$r^2 = \frac{1}{n_1 n_2} \frac{(s_1 n_2 - s_2 n_1)^2}{(n_1 + n_2)(q_1 + q_2) - (s_1 + s_2)^2} = \frac{s_1^2/n_1 + s_2^2/n_2 - G}{q_1 + q_2 - G},$$

wherein a factor G can be introduced, which results in a numeric simplification of the computation:

$$G := \frac{(s_1 + s_2)^2}{n_1 + n_2}$$

The present apparatus has a selection and actuating unit 14, using which one or more electrodes 21 among the electrodes preselected by the analysis unit can be selected to emit a predefined electrical stimulus S. The selection and actuating unit 14 is connected downstream of the analysis unit 13 and is connected upstream of the stimulation unit 11. In the present preferred exemplary embodiment of a selection and actuating unit 14, which is shown in FIG. 8, the selection and actuating unit 14 has a display unit 141, which represents the electrodes 21 and the analysis results ascertained by the analysis unit 13, in particular in the present case the preselection results ascertained on the basis of the correlation coefficient k, preferably by threshold value comparison, on the basis of the analysis for the individual electrodes 21 at positions 142 of the display unit in the form of graphic visualizations 143a, 143b. The illustrated selection and actuating unit 14 has individual selection and actuating elements 144 for each individual electrode 21 in the region of the display unit 141. The selection and actuating elements 144 are each associated with one electrode 21 and are arranged on the display unit 141 in the region of the position 142, at which the graphic visualizations 143a, 143b for the relevant electrode 21 are also shown. The selection and actuating elements 144 are designed for selecting the electrode 21 associated with them for the emission of a stimulus S or for the emission of a stimulus S using the relevant electrode 21. A particularly preferred selection of electrodes 21 by the selection and actuating unit 144 is carried out by also selecting an adjacent electrode 21 upon selection of a respective electrode 21. A stimulus S is emitted in the form of a current between the two electrodes 21 thus selected. If one electrode 21 is preselected by the selection and actuating unit 14 as a result of the analysis, the selection and actuating unit 14 thus proposes an electrode 21 adjacent to this selected electrode 21 for selection or selects it itself. Upon actuation, a stimulus S in the form of a current is emitted between these two electrodes 21. It is also advantageous that multiple electrodes 21 can be stimulated simultaneously or in rapid succession, in order to amplify the effect and make the mapping faster.

The emitted electrical stimulus S preferably has a DC component which is below a predefined threshold value. This can be carried out in that the stimulation unit 11 applies a DC-free stimulus S to the electrodes 21. Alternatively, the DC component can also be reduced in that the stimulus 21 is chronologically limited. In both cases, square-wave pulses can be used for the stimulation, for example, having a duration of 1 ms and a current strength of 10 mA.

For stimulation using different stimulation threshold values, it can particularly advantageously be provided that the stimulation unit 11 is designed for the purpose of applying stimuli S of different and rising strengths to the individual electrodes 21. The stimulation unit 11 can also be designed to emit the individual stimuli S upon manual actuation.

Alternatively, however, the possibility also exists that the stimulation unit 11 is activated to emit stimuli in rising sequence until a registration unit 22 establishes or registers a reaction of the test subject 3. The registration unit 22 is connected to the control unit and can be formed, for example, by a microphone for registering speech of the test subject 3 or by a detector for registering movements of the test subject 3. The registration unit 22 can also be replaced by a manual actuation, by the physician registering the reaction of the test subject and ending the stimulation accordingly.

In addition, the possibility also exists of detecting discharges after the stimulation (after discharges). They are triggered by the electrostimulation in the brain and indicate that an epileptic seizure is possibly imminent. In such a case, it can be provided that the current used for the electrostimulation is not elevated further and/or the stimulation is ended. The physician is notified of the after discharges by a warning.

If such a discharge (after discharge) is recognized, the possibility exists of emitting further stimuli to manually suppress an epileptic seizure.

In a further advantageous embodiment of the invention, the possibility exists of directly displaying the individual intermediate results ascertained in the course of the analysis of the measurement signals or the individual measurement data.

Furthermore, the possibility exists of displaying spectral information of the ascertained raw measurement data, in particular to be able to recognize disturbances early. In addition, the possibility exists that individual electrodes which only have poor contact or are damaged overall are excluded from the measurement. No measurement data are then collected overall for such electrodes and no analysis is also carried out for such electrodes.

In a further preferred embodiment of the invention, the possibility exists that the signal ground can be selected arbitrarily or can be placed at an arbitrary voltage value.

This is advantageous in particular to avoid a measurement becoming impossible if the ground used during the measurement is subject to interference.

In principle, the possibility exists that a variety of different mental activities can be specified to the test subject, for example, solving a Rubik's cube, hearing exercises, naming images, kissing movements, tongue movements, reading, computing, reminiscences, etc. The possibility also exists in this case that different activities can be repeated to obtain better quality of the recordings overall. In addition, the possibility also exists that the quality of individual recordings is displayed. The number of the mental activities which are specified to a human does not necessarily need to be restricted. The possibility also exists that additional intellectual activities are specified by the test subject or by the investigator.

Further possibilities for producing measurement signals in different states of the human brain are to stimulate the body in a tactile, auditory, or visual manner.

In addition, it is also possible to print out and store individual analysis results and the entirety of all analysis results at the end of the measurement.

In addition, the possibility also exists of noting in the individual stored results between which electrodes or at which electrodes automatic or manual stimulations are performed. Such stimulations can be noted in the individually stored or printed measurement results.

A further embodiment enables cortical networks to be recognized by stimulating a known brain region by means of two electrodes (21), preferably at 1-50 Hz. Evoked potentials are computed and possibly visualized at all other electrodes. These can be ascertained by event-related averaging with trend and baseline correction. The advantage is that using this procedure, only a single region, for example, Broca's area, has to be stimulated to recognize the entire speech network of the brain. High-gamma mapping is used as the foundation for this purpose, to recognize a specific brain region which is subsequently electrically stimulated to recognize the network.

A further special feature, in addition to the evoked potential or instead of the evoked potential, is also that the band power in the range of 60-1000 Hz can be computed, in order to detect cortical networks in this manner, for example, the speech network, by high-gamma analysis.

The invention claimed is:

1. An apparatus for electro stimulation of a test subject, the apparatus comprising:
   a plurality of electrodes applicable to a human brain for applying an electrical stimuli on the human brain;
   a control unit containing:
   a stimulation unit for applying the electrical stimuli to individual or multiple ones of said electrodes;
   a measuring unit connected downstream of said electrodes for determining voltages applied to said electrodes;
   an analysis unit for analyzing individual measurement signals registered using said electrodes as measuring electrodes;
   a reference memory;
   said control unit being configured to carry out a base measurement by means of said analysis unit, during which the test subject executes a reference activity, and to store analysis results, associated with a respective measuring electrode of said measuring electrodes, ascertained as stored reference values or stored reference signal in said reference memory and keep the analysis results available;
   said analysis unit having a comparison unit for comparing individual ascertained analysis values to the stored reference values, wherein an analysis result for each of said electrodes specifies how much the individual ascertained analysis values differ from the stored reference values associated with said respective measuring electrode;
   said analysis unit configured for preselecting individual ones of said electrodes for an emission of a stimulus on a basis of the analysis of registered measurement signals;
   a selection and actuating unit, being actuatable, for selecting at least one of said electrodes among said electrodes preselected by said analysis unit and also for an emission of a predefined electrical stimulus by said stimulation unit on said at least one electrode selected by said analysis unit, which is connected downstream of said analysis unit and is connected upstream of said stimulation unit; and
   said analysis unit configured for examining the measurement signals at said measuring electrodes, during the preselection, for a presence of signal powers or signal energies in a range of 60 Hz to 1 kHz.

2. The apparatus according to claim 1, wherein said selection and actuating unit has a display unit for displaying said electrodes and also analysis results ascertained by said analysis unit on a basis of an analysis for said electrodes at positions of said display unit in as graphic renderings of the analysis results.

3. The apparatus according to claim 2, wherein:
   said selection and actuating unit has individual selection or actuating elements in a region of said display unit;
   said individual selection or actuating elements are each associated with one of said plurality of electrodes and are disposed on said display unit in the region of a position at which the graphic renderings for each respective electrode of said plurality of electrodes are represented; and
   said individual selection or actuating elements are configured for selecting said electrode associated therewith for the emission of the stimulus or for the emission of the stimulus using said respective associated electrode.

4. The apparatus according to claim 1, wherein said selection and actuating unit enables a selection of said electrode preselected by said analysis unit and an adjacent electrode adjacent thereto, said stimulation unit is configured to emit the stimulus as a current between said electrode and said adjacent electrode, wherein a DC component of the current flowing as the stimulus between said electrode and said adjacent electrode is below a predefined threshold value, wherein:
   a) said stimulation unit applies a DC-free stimulus to said electrodes; or
   b) said stimulation unit limits the DC component of the current of the stimulus, and a current curve of the stimulus has a square, triangular, or sinusoidal curve.

5. The apparatus according to claim 1, further comprising a registration unit for registering a reaction of the test subject and connected to said control unit, said registration unit has a microphone for registering speech of the test subject or a detector for registering movements of the test subject or electrophysiological signals.

6. The apparatus according to claim 5, wherein said stimulation unit is configured to apply the stimuli with differing strengths and/or durations to said electrodes, wherein:
   a) said stimulation unit is configured to emit the stimuli upon manual actuation or automatically; or
   b) said control unit activates said stimulation unit to emit the stimuli in a rising sequence until said registration unit establishes a reaction of the test subject or a current limit is reached.

7. The apparatus according to claim 1, wherein said electrodes are disposed in at least one grid, wherein said electrodes are disposed within a respective grid in a predefined structure, and/or each of said electrodes except for edge electrodes of said electrodes has a predefined number of adjacent electrodes, which are disposed at a predetermined position in relation to the respective electrode and/or have equal spacing from one another.

8. The apparatus according to claim 7, wherein:
said electrodes are formed equivalently in relation to one another; and/or
said electrodes disposed within said at least one grid are formed equivalently in relation to one another; and/or
said electrodes within said grid are disposed in a square or hexagonal structure.

9. The apparatus according to claim 1, further comprising a separate filter connected downstream of said electrodes, said filter is connected upstream of said analysis unit or said measuring unit and is configured:
a) such that if signal energy which exceeds or falls below a predefined threshold value or a signal form deviating from a setpoint form by more than a predefined threshold value is present, to suppress a relevant signal and not relay the relevant signal to said analysis unit; and/or
b) to filter out signal components below a limiting frequency of 1 Hz to 5 Hz; and/or
c) to subtract a mean value of all simultaneously measured signal values of all said electrodes from a measured value of a relevant electrode;
d) to subtract a weighted mean value of all the simultaneously measured signal values of all adjacent electrodes of said relevant electrode from the measured value of the relevant electrode, wherein in a square grid of said electrodes, the following are adjacent electrodes:
i) said four electrodes directly adjoining said relevant electrode;
ii) said eight electrodes surrounding said relevant electrode, wherein said adjacent electrodes are weighted with a weighting factor dependent on a distance thereof from said relevant electrode; and
iii) those said four electrodes within the square grid, a coordinate position of which deviates by two from a relevant coordinate position of said relevant electrode, and an other coordinate position of which corresponds to a relevant coordinate position of said relevant electrode.

10. The apparatus according to claim 1, wherein:
said analysis unit is configured to produce continuously derived measured values for each of said electrodes, the measured values produced within a predefined period of time are combined into windows having a length of 20 ms to 2 seconds;
said analysis unit is configured, by means of fast Fourier transform (FFT) or autoregressive models, to ascertain signal energy of a signal within a window in a frequency range having a lower frequency of 60 to 100 Hz and an upper frequency in a frequency range of 150 to 1 kHz, and to produce an analysis signal therefrom, and to produce a reference signal in a scope of the base measurement; and
said analysis unit does not use frequency ranges within a predefined window, which lie in a range around a network frequency or a multiple of the network frequency for a formation of the signal energy.

11. The apparatus according to claim 1, wherein:
said control unit is configured to emit the stimulus in a region of said electrode using a voltage stimulus having a frequency between 1 Hz and 100 Hz;
said control unit is configured, after the emission of the stimulus at all or a number of said electrodes to:
a) detect evoked potentials in an emitted signal of said respective electrode; or
b) detect a band power of the emitted signal of said respective electrode, in a range between 60 Hz and 1 kHz; and
said control unit depicts all of said electrodes or brain regions registered by said electrodes in a manner in which an evoked potential or an elevated band power in a range between 60 Hz and 1 kHz exists as a result of the stimulus.

12. A method for electro stimulation of a test subject, which comprises the steps of:
applying a plurality of electrodes to a brain of the test subject;
carrying out a base measurement, during which the test subject executes a reference activity, and analysis results ascertained are associated with a respective electrode and stored as stored reference values or as a reference signal and kept available;
specifying different mental activities to the test subject and voltages applied at the electrodes are measured and analyzed;
comparing individual ascertained analysis values to the stored reference values for ascertaining for each individual ones of the electrodes how much the individual ascertained analysis values differ from the stored reference values associated with the respective electrode;
preselecting individual ones of the electrodes for an emission of a stimulus on a basis of an analysis;
selecting one of the individual preselected electrodes and the stimulus is emitted to the brain using the one electrode; and
studying, in an analysis used during a preselection of measurement signals, signals applied at the electrodes for a presence of signal powers or signal energies in a range of 60 Hz to 1 kHz.

13. The method according to claim 12, wherein the electrodes selected in a course of the preselection are graphically displayed.

14. The method according to claim 12, which further comprises emitting the stimulus as a current between the selected electrode and an adjacent electrode adjacent to the selected electrode, wherein a DC component of the current flowing between the adjacent electrode and the selected electrode as a stimulus is below a predefined threshold value, where:
a) the stimulus is DC-free; or
b) a direct component of the current of the stimulus is limited, and a current curve of the stimulus has a square, triangular, or sinusoidal curve.

15. The method according to claim 12, which further comprises registering a reaction of the test subject by a microphone for registering speech of the test subject or by a detector for registering movements of the test subject or for registering electrophysiological signals.

16. The method according to claim 12, which further comprises applying the stimuli in a rising strength and/or duration to the electrodes, wherein:
the stimuli are emitted upon manual actuation or automatically; or
the stimuli are emitted in a rising sequence until a registration unit establishes a reaction of the test subject or a maximum stimulus is reached or a current limit is reached.

17. The method according to claim 12, which further comprises disposing the electrodes in at least one grid, the electrodes within a respective grid are disposed in a predefined structure, and/or each of the electrodes except for edge electrodes has a predefined number of adjacent electrodes which are disposed at a predetermined position in relation to the respective electrode and/or have equal spacing from one another.

18. The method according to claim 17, wherein:
the electrodes are formed equivalently in relation to one another; and/or
the electrodes disposed within the at least one grid are formed equivalently in relation to one another; and/or
the electrodes within the grid are disposed in a square or hexagonal structure.

19. The method according to claim 17, which further comprises filtering individual measured values of the electrodes, wherein:
a) if a signal energy which exceeds or falls below a predefined threshold value or a signal form deviating from a setpoint form by more than a predefined threshold value is present, a relevant signal is suppressed and not relayed to the analysis unit; and/or
b) signal components below a limiting frequency of 1 Hz to 5 Hz are filtered out; and/or
c) a mean value of all simultaneously measured signal values of all the electrodes, only within the at least one grid, is subtracted from a measured value of a relevant electrode;
d) a weighted mean value of all the simultaneously measured signal values of all adjacent electrodes of the relevant electrode, only within the grid, is subtracted from the measured value of the relevant electrode, wherein in a square grid of the electrodes, the following are adjacent electrodes:
i) the four electrodes directly adjoining the relevant electrode;
ii) the eight electrodes surrounding the relevant electrode, wherein the adjacent electrodes are weighted with a weighting factor dependent on a distance thereof from the relevant electrode; and
iii) the four electrodes within the square grid, one coordinate position of which deviates by two from a relevant coordinate position of the relevant electrode, and an other coordinate position of which corresponds to a relevant coordinate position of the relevant electrode.

20. The method according to claim 12, wherein:
continuously derived measured values are produced for each of the electrodes, wherein the measured values produced within a predefined period of time are combined into windows having a length of 20 ms to 2 seconds by means of FFT or autoregressive models, and signal energy of a signal is ascertained within a window in a frequency range having a lower frequency of 60 to 100 Hz and an upper frequency in a frequency range of 150 Hz to 1 kHz, and an analysis signal is produced therefrom, and a reference signal is produced in a scope of the base measurement; and
frequency ranges within a predefined window, which lie in a range around a network frequency or a multiple of the network frequency, are not used for a formation of the signal energy.

21. The method according to claim 12, which further comprises emitting the stimulus in a region of the electrode, namely a voltage stimulus having a frequency between 1 Hz and 100 Hz, and after an emission of the stimulus at all or a number of the electrodes:
a) detecting evoked potentials, or
b) detecting a band power in a range between 60 Hz and 1 kHz, and all the electrodes or brain regions registered by the electrodes are displayed and/or kept available, in which an evoked potential or an elevated band power in a range between 60 Hz and 1 kHz was ascertained as a result of the stimulus.

22. A non-transitory data carrier having computer executable instructions for performing a method for electro stimulation of a test subject, which comprises the steps of:
applying a plurality of electrodes to a brain of the test subject;
carrying out a base measurement, during which the test subject executes a reference activity, and analysis results ascertained are associated with a respective measuring electrode of the plurality of electrodes and stored as stored reference values or as reference signal and kept available;
specifying different mental activities to the test subject and voltages applied at the electrodes are measured and analyzed;
comparing individual ascertained analysis values to the stored reference values for ascertaining for each individual ones of the electrodes how much the individual ascertained analysis values differ from the stored reference values associated with a respective electrode;
preselecting individual ones of the electrodes for an emission of a stimulus on a basis of the analysis;
selecting one of the electrodes from the individual preselected electrodes and a stimulus is emitted to the brain using the one electrode; and
studying, in an analysis used during a preselection measurement signals, signals applied at the electrodes for a presence of signal powers or signal energies in the range of 60 Hz to 1 kHz.

* * * * *